United States Patent [19]

Rosenberg

[11] Patent Number: 4,610,253
[45] Date of Patent: Sep. 9, 1986

[54] METHOD AND APPARATUS FOR THE PREVENTION OF PRESSURE SORES

[75] Inventor: Lior Rosenberg, Omer, Israel

[73] Assignee: Brig Research Ltd., Los Angeles, Calif.

[21] Appl. No.: 637,270

[22] Filed: Aug. 3, 1984

[30] Foreign Application Priority Data

Aug. 19, 1983 [IL] Israel ......................................... 69528

[51] Int. Cl.⁴ ........................... A61N 0/00; H05C 3/00
[52] U.S. Cl. .................................... 128/382; 128/905;
128/133; 128/134; 128/135; 128/68.1;
128/82.1; 128/378; 128/594
[58] Field of Search .............. 128/133, 134, 135, 68.1,
128/82.1, 378, 382, 905, 594

[56] References Cited

U.S. PATENT DOCUMENTS

| 4,217,705 | 8/1980 | Donzis | 128/594 |
| 4,458,430 | 7/1984 | Peterson | 128/594 |
| 4,472,890 | 9/1984 | Gilbert | 128/594 |

Primary Examiner—Herbert S. Cockeram
Attorney, Agent, or Firm—Benjamin J. Barish

[57] ABSTRACT

A method and apparatus for the prevention of pressure sores at an unfeeling part of a person's body involves applying to the unfeeling part of the person's body a pressure-sensor cell which senses the pressure thereat, applying to a feeling part of the person's body a discomfort-generator cell, and connecting the pressure-sensor cell to the discomfort-generator cell such that the pressure sensed by the former at the unfeeling part of the person's body is transmitted by the latter to the feeling part of the person's body.

18 Claims, 7 Drawing Figures

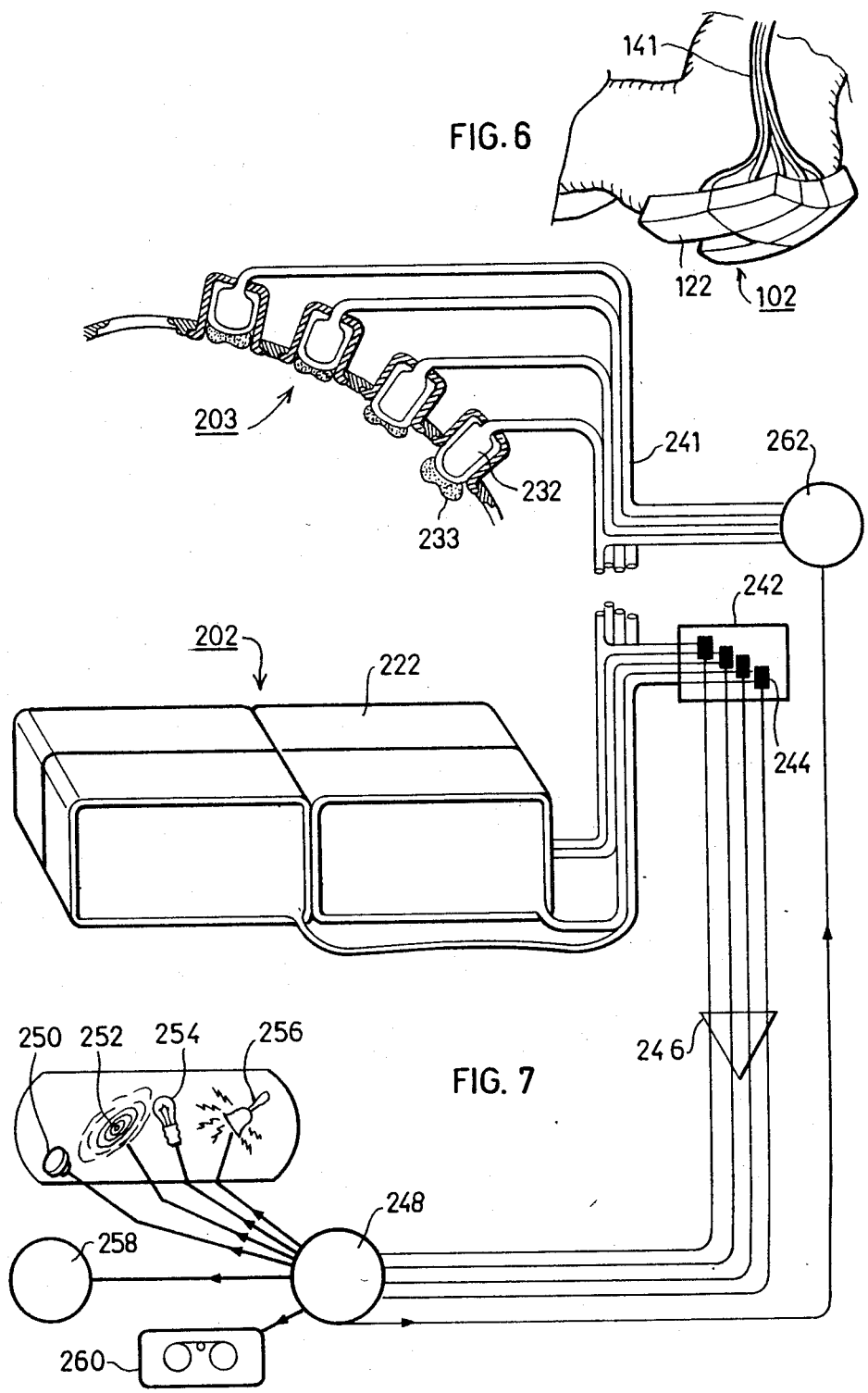

METHOD AND APPARATUS FOR THE PREVENTION OF PRESSURE SORES

BACKGROUND OF THE INVENTION

The present invention relates to a method and apparatus for the prevention of pressures sores.

Pressure sores, such as bedsores or decubitus ulcers, are caused by the continuous pressure of a bed, chair, shoe, or the like on an unfeeling or uninnervated part of a person's body. Such sores are slow and difficult to heal, and present a serious danger to persons who are subjected to sensory loss of a part of their body as a result of, for example, vascular damage or neural damage. Thus, normal persons will start to feel pain when subjected to continuous local pressure and will therefore shift their body automatically to lessen the discomfort, but patients having a sensory loss are deprived of this protection and are therefore common victims of pressure sores. Heretofore, the most common way of reducing the formation of such sores was to provide padding for the affected area, or periodically to move the patient in order to prevent the continuous application of the pressure to the discrete unfeeling points on his body.

SUMMARY OF THE INVENTION

An object of the present invention is to provide a novel method and apparatus for the prevention of pressure sores.

According to one broad aspect of the present invention, there is provided a method for the prevention of pressure sores at a natural unfeeling part of a person's body, comprising: applying to the unfeeling part of the person's body a pressure-sensor which senses the pressure applied thereto; applying to a feeling part of the person's body a discomfort-generator; and connecting the pressure-sensor to the discomfort-generator such that the pressure sensed by the pressure-sensor at the unfeeling part of the person's body is transmitted by the discomfort-generator as a discomfort to the feeling part of the person's body.

In the preferred embodiment of the invention described below, the pressure sensor includes a plurality of fluid-filled pressure-sensor cells applied to the unfeeling part of the person's body at discrete points thereof and invidually connected to a plurality of fluid-filled discomfort-generator cells applied to discrete points of the feeling part of the person's body.

The invention also provides apparatus for carrying out the above method.

The invention thus exploits the natural biofeedback mechanism of a person's body to cause the person to change position in order to reduce pain or nagging pressure. That is, a person who feels pain or nagging pressure anywhere on his body will very quickly learn to shift his weight or position in the best manner to secure relief. For example, a paraplegic patient quickly learns that the discomfort caused by the transmission of the pressure from an unfeeling part of his body (e.g., his buttocks) to a feeling part of his body (e.g., his arm) will be relieved only if he changes his position (i.e., his sitting posture) in a certain direction such that this discomfort at to the feeling part of his body is relieved. The invention thus causes the patient himself to make the movements which will relieve the pressure sensations on the feeling part of his body and which, thereby, will also prevent the formation of pressure sores on the unfeeling part of his body.

The invention may also include active devices which actuate signals or control other devices in response to sensing a pressure exceeding a predetermined magnitude and/or time interval at the unfeeling part of the patient's body. For example, the apparatus could energize a device which redistributes the fluid in the plurality of pressure-sensor cells to thereby redistribute the forces applied by them to the unfeeling part of the person's body, and thus actually produce the movement of the person's body preventing the formation of the pressure sores.

Further features and advantages of the invention will be apparent from the description below.

BRIEF DESCRIPTION OF THE DRAWINGS

The invention is herein described, by way of example only, with reference to the accompanying drawings, wherein:

FIGS. 4 and 5 and 6 illustrate a second embodiment of the invention for application to the buttocks of a person; and FIG. 7 illustrates the embodiment of the invention in FIGS. 4-6, equipped with means for controlling various types of devices in response to sensing a pressure of a predetermined magnitude or time duration.

DESCRIPTION OF PREFERRED EMBODIMENTS

Figure 1:
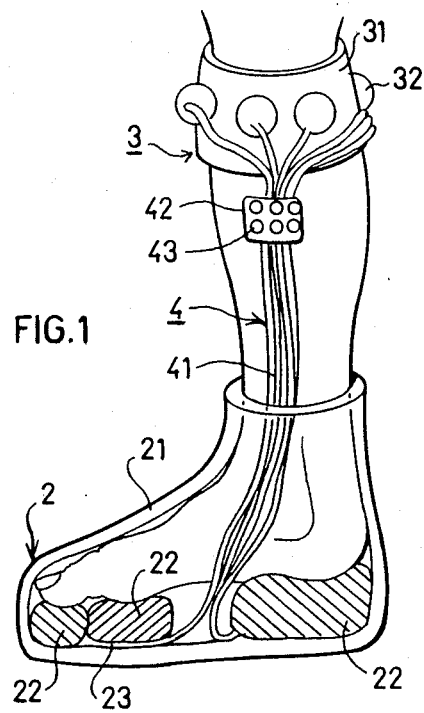
FIGS. 1 and 2 illustrate one embodiment of the invention for application to the foot of a person.
Figure 2:
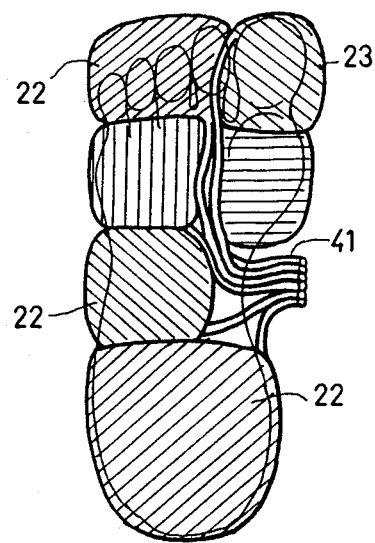
Figure 3:
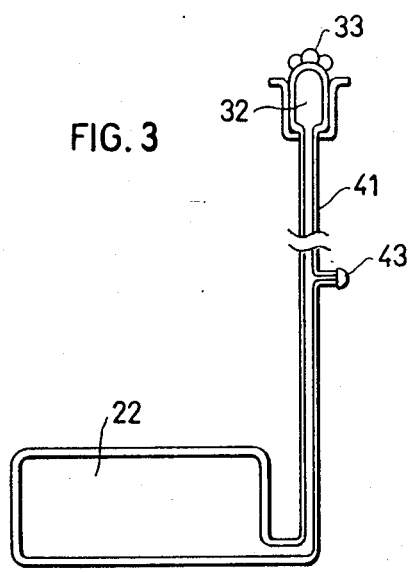
FIG. 3 illustrates the main parts of the device of FIGS. 1 and 2.

The embodiment of the invention illustrated in FIGS. 1-3 is particularly applicable for a person suffering from an ailment wherein the bottom of his foot is insensitive to pressure and therefore must be protected against pressure sores. The apparatus includes a pressure-sensor device 2 to be applied to the unfeeling part of the person's body, namely the underside of his foot; a discomfort-generator device 3 to be applied to a feeling part of the person's body, in this case a higher part of the person's leg; and a connecting device 4 connecting the pressure-sensor 2 to the discomfort-generator 4. The arrangement is such that the pressures at the unfeeling part of the person's body, namely the underside of his foot occupied by the pressure-sensor 2, are transmitted to a feeling part of the person's body, namely the portion of his leg enclosed by the discomfort-generator 3.

More particularly, the pressure-sensor 2 is in the form of a sock 21 adapted to be applied over the patient's foot, and includes a pad constituted of a plurality of liquid-filled cells 22 lining the bottom of the sock. The various cells 22 of the pad can be individually configured according to the distribution of the load on the foot, as shown particularly in FIG. 2. In this example, there are six such liquid-filled cells 22, each constituted of a flexible wall 23 of rubber or plastic sheet material defining an expansible and contractible chamber filled with a liquid, such as water.

The discomfort-generator 3 is in the form of a band 31 applied to the upper portion of the person's foot and including a plurality of liquid-filled cells 32 disposed in a circular array around the band. The number of cells 32 in the discomfort-generator 3 corresponds to the number of cells 22 in the pressure-sensor 2, one cell of each being connected to a cell of the other by means of a fluid conduit 41 in the connecting device 4. Each cell 32 is inflated when subjected to pressure from its respective cell 22, and preferably includes a rigid element 33, (FIG. 3) which is pressed against the patient's skin to apply thereto a pressure sensation corresponding to the magnitude and duration of the pressure applied to its cell 22.

It will thus be seen that pressure applied to the cells 22 of the pressure-sensor 2 at the underside of the foot will be transmitted via their respective tubes 41 to the corresponding cells 32 in the discomfort-generator 3. In this manner, pressure at the unfeeling part of the person's body (the underface of the foot in FIGS. 1 and 2) are transferred by the connecting tubes 21 and cells 32 to a feeling part of the person's body (the upper part of the person's leg). The person, when feeling this pain or nagging pressure at the upper part of his leg, will very quickly learn to shift his weight in the best manner to relieve this discomfort, thereby preventing the formation of pressure sores at this underface of his foot even though he has no pressure sensation there.

The connecting device 4, between the pressure-sensor 2 and the pressure-generator 3, preferably includes a fitting 42 providing a port 43 for each of the connecting tubes 41. Ports 43 may thus be connected to an external device, such as a signal, alarm, or control, as will be described below particularly with reference to FIG. 7.

Figure 4:
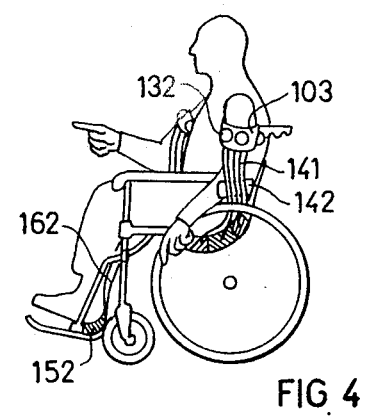
Figure 5:
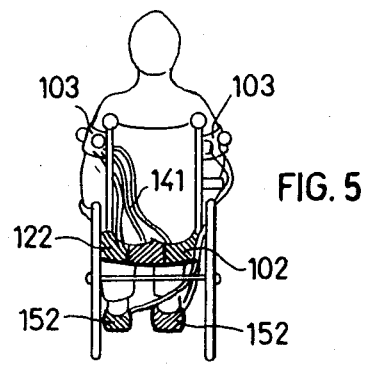

FIGS. 4-6 illustrate another embodiment of the invention for use in preventing the formation of pressure sores on the buttocks of a person who may be confined to a wheelchair. In this case, the pressure-sensor 102 is in the form of a seat pad having a plurality of individual cells 122 filled with liquid such as water, this pad being configured to underlie the patient's seat or buttocks. In this embodiment, the discomfort-generator 103 is also in the form of a band, but here the band is applied to the upper part of the patient's arm, or any other part of the patient's arm or body which can feel pressure sensations. The plurality of cells 122 in the pressure-sensor pad 102 are connected to the corresponding cells 132 in the discomfort-generator band 103 by individual tubes 141. Thus, the pressures at any point of the person's buttocks (the unfeeling part of the person's body to be protected against the formation of pressure sores) are transmitted via tubes 141 and cells 132 to a feeling part of the person's body (his arm) so as to cause him to move his buttocks in order to relieve this discomfort, which thereby prevents the formation of pressure sores on his buttocks.

It will be appreciated that the apparatus could include more than one pressure-sensor at different unfeeling parts of the body connected to the discomfort-generator device at a feeling part of the body. This is shown in FIG. 4, for example, wherein an additional pressure-sensor cell 152 is provided to underlie each heel, which cell is connected by a tube 162 to one of the cells 132 in the discomfort-generator band 103. As indicated earlier, the patient quickly learns what kind of movement he should make in order to relieve him from the discomfort caused to a particular feeling part of his body; and therefore, whenever he finds that moving his buttocks or heel will relieve a particular discomfort, he will quickly learn to move the appropriate part of his body when such a discomfort is produced.

The connecting tubes 141 in this embodiment also preferably include a fitting 142 having a plurality of ports enabling connections to be made to an external signalling, alarm, or control device, as mentioned with respect to the FIGS. 1-3 embodiment.

FIG. 7 schematically illustrates a number of controls that could be incorporated in the appratus of either FIGS. 1-3 or FIGS. 4-6. Thus, as shown in FIG. 7, the pressure-sensor 202 is in the form of a pad similar to pad 102 in the FIGS. 4-6 embodiment, and each of the cells 222 of the pad is connected by an individual tube 241 to a cell 232 of the discomfort-generator 203. The latter device may also be in the form of a band to enclose a feeling part of a leg or arm of the patient. Each cell 232 carries a rigid member 233 on the side of the band engaging the skin of the patient, and presses that member against the skin when its respective cell 232 is inflated by the transmission of pressure from the pressure-sensor pad 202 to one of the cells 232 of the discomfort generator band 203.

The arrangement illustrated in FIG. 7 further includes a fitting 242 provided with a plurality of ports each covered by a pressure transducer 244 which converts the pressure at the respective port to an electrical signal. These electrical signals are amplified in an amplifier 246 and fed to a processor 248, which processes them according to the particular application. For example, the signals could be processed so as to actuate an electrical indicator 250, a vibrator 252, a visual alarm 254, and/or an audio alarm 256. Processor 248 could also be connected to a display unit 258, or to a recorder 260.

FIG. 7 further illustrates processor 248 also controlling a drive device 262 connected to the cells 222 of the pressure-sensor pad 202. Thus, processor 248 could be programmed to perform, among its other functions, the further function, upon sensing a pressure of predetermined magnitude and/or predeterminded time interval, of actuating drive 262 to redistribute the forces applied by these cells to the unfeeling part of the person's body, causing the cells to shift the person's body. Thus, the apparatus does not rely only on the natural biofeedback mechanism of the person for shifting his body when subjected to a nagging pressure or pain, but rather effects the shifting automatically itself, and thereby prevent pressure sores.

It will be appreciated that the pad could be in the form of a mattress for protecting the patient while lying, and that many other variations, modifications, and applications of the invention may be made.

What is claimed is:

1. A method for the prevention of pressure sores at a naturally unfeeling part of a person's body, comprising: applying to said unfeeling part of the person's body a pressure-sensor which senses the pressure applied thereto; applying to a feeling part of the person's body a discomfort-generator; and connecting said pressure sensor to said discomfort-generator such that the pressure sensed by said pressure-sensor at the unfeeling part of the person's body is transmitted by said discomfort-generator as a discomfort to the feeling part of the person's body.

2. The method according to claim 1, wherein said pressure-sensor includes a plurality of cells which are applied to the unfeeling part of the person's body at discrete points thereof, and said discomfort-generator includes a plurality of other cells applied to discrete points of the feeling part of the person's body and individually connected to said pressure-sensor cells.

3. The method according to claim 2, wherein said pressure-sensor cells are connected by fluid connections to said discomfort-generator cells.

4. The method according to claim 2, including the further step of determining when the unfeeling part of the person's body has been subjected to a pressure of predetermined magnitude and/or time duration, and actuating a control device in response thereto.

5. The method according to claim 4, wherein said plurality of sensor cells is filled with a fluid, and said control device is effective to redistribute the fluid in said plurality of sensor cells, and thereby to redistribute the forces applied by them to the unfeeling part of the person's body.

6. Apparatus for the prevention of pressure sores at a naturally unfeeling part of a person's body, comprising: a pressure-sensor applicable to said unfeeling part of the person's body for sensing a pressure applied thereto; a discomfort-generator applicable to a feeling part of the person's body; and a connection between said pressure sensor and said discomfort-generator, such that the pressure sensed by said pressure-sensor at the unfeeling part of the person's body is transmitted by said discomfort-generator as a discomfort to the feeling part of the person's body; said pressure-sensor including a plurality of fluid-filled cells for application to the unfeeling part of the person's body at discrete points thereof, and said discomfort-generator including a plurality of other cells applied to discrete points of the feeling part of the person's body and individually connected to said pressure-sensor cells to generate pressures at discrete points of the feeling part of the person's body in response to the pressures sensed at the unfeeling part of the person's body.

7. Apparatus according to claim 6, wherein said pressure-sensor cells are connected by fluid connections to said pressure-generator cells.

8. Apparatus according to claim 6, further including means determining when said unfeeling part of the person's body has been subjected to a pressure of a predetermined magnitude and/or time duration, and means for energizing a control device in response thereto.

9. Apparatus according to claim 8, wherein said control device includes means effective to redistribute the fluid in the plurality of pressure-sensor cells, and thereby to redistribute the forces applied by them to the unfeeling part of the person's body.

10. Apparatus according to claim 6, wherein said pressure-sensor cells are incorporated in a pad engageable with and supporting said unfeeling part of the person's body.

11. Apparatus according to claim 10, wherein said pad is configured for application to the underface of the person's foot.

12. Apparatus according to claim 10, wherein said pad is configured for application to the underface of a person's buttocks.

13. Apparatus according to claim 6, wherein said pressure-generator cells are incorporated in a band to enclose a part of the limb of the person.

14. Apparatus for the prevention of the formation of pressure sores on an unfeeling part of a person's body, comprising:
   a pad including a plurality of fluid-filled cells supporting said unfeeling part of the person's body;
   sensor means sensing when said unfeeling part of the person's body has been subjected to a pressure of predetermined magnitude and/or time duration;
   and redistribution means automatically controlled by said sensor means for redistributing the fluid in said plurality of cells, and thereby for redistributing the forces applied by them to said unfeeling part of the person's body.

15. Apparatus according to claim 14, wherein said plurality of cells are filled with a liquid.

16. Apparatus according to claim 14, further including a second plurality of fluid-filled cells attachable to engage a feeling part of the person's body, and a plurality of tubes individually connecting said latter cells with said pad cells to transfer pressures at the unfeeling part of the person's body to the feeling part of the person's body.

17. Apparatus according to claim 16, wherein said pressure-sensor cells are connected by fluid connections to said pressure-generator cells.

18. Apparatus according to claim 17, wherein the fluid in all said cells and in said connections is a liquid.

* * * * *